(12) United States Patent
Lambert

(10) Patent No.: US 7,835,882 B2
(45) Date of Patent: Nov. 16, 2010

(54) METHOD OF ANALYSIS AND AN ANALYZER

(75) Inventor: Noel William Alexander Lambert, Lower Belford (AU)

(73) Assignee: Newcastle Innovation Limited, Callaghan (AU)

( * ) Notice: Subject to any disclaimer, the term of this patent is extended or adjusted under 35 U.S.C. 154(b) by 0 days.

(21) Appl. No.: 12/067,629

(22) PCT Filed: Sep. 20, 2006

(86) PCT No.: PCT/AU2006/001376

§ 371 (c)(1),
(2), (4) Date: Jul. 2, 2008

(87) PCT Pub. No.: WO2007/033415

PCT Pub. Date: Mar. 29, 2007

(65) Prior Publication Data

US 2008/0262783 A1  Oct. 23, 2008

(30) Foreign Application Priority Data

Sep. 20, 2005  (AU) .............................. 2005905188

(51) Int. Cl.
*G01N 9/36* (2006.01)
(52) U.S. Cl. ............................ 702/137; 209/166; 588/1
(58) Field of Classification Search ................... 702/25, 702/30, 136, 137; 209/3.2, 160; 73/19.05; 378/45, 47; 588/1
See application file for complete search history.

(56) References Cited

U.S. PATENT DOCUMENTS 4,726,896 A * 2/1988 Grove et al. ............. 209/166
5,414,195 A * 5/1995 Peterson et al. ........... 588/1

FOREIGN PATENT DOCUMENTS

| DE | 19724798 | | 12/1998 |
|----|----------|---|---------|
| JP | 61-164142 | | 7/1986 |
| JP | 03-240445 | | 11/1991 |
| JP | 03-246445 | | 11/1991 |
| JP | 2001328877 A | * | 11/2001 |
| JP | 2002-205097 | | 7/2002 |
| SU | 968702 | | 10/1982 |

OTHER PUBLICATIONS

International Search Report prepared by the Australian Patent Office in regard to International Application No. PCT/AU2006/001376 (3 pages).
International Preliminary Report on Patentability prepared by the Australian Patent Office in regard to International Application No. PCT/AU2006/001376 (4 pages, Nov. 8, 2006).

* cited by examiner

*Primary Examiner*—John H Le
(74) *Attorney, Agent, or Firm*—Marshall, Gerstein & Borun LLP

(57) ABSTRACT

The present invention provides a method of online analysis of mineral waste content of a slurry in a mineral separation process, said method including the steps of: measuring the density of said slurry (10); measuring the concentration of solids in said slurry (12); calculating the density of solids in said slurry from said slurry density and said solids concentration (20); and calculating said mineral waste content from said solids density (22). The present invention also provides an online analyzer for mineral waste content of a slurry in a mineral separation process.

56 Claims, 5 Drawing Sheets

METHOD OF ANALYSIS AND AN ANALYZER

FIELD OF THE INVENTION

The present invention relates to a method of analysis and an analyser. In particular, the invention relates to a method of online analysis of and an online analyser for mineral waste content.

The invention has been developed primarily for use in analysing the mineral waste content of a slurry online in a coal separation process, and will be described hereinafter with reference to this application. However, it would be appreciated that the invention is not limited to this particular field of use. In particular, it is contemplated that the invention is applicable to a separation process for any mineral, including iron ore, copper and lead. The invention is generally applicable to any separation process on the basis of density, such as the recycling of garbage.

BACKGROUND OF THE INVENTION

Any discussion of the prior art throughout the specification should in no way be considered as an admission that such prior art is widely known or forms part of the common general knowledge in the field.

Coal separation involves the use of coarse circuits to remove coarse waste and fines circuits to remove fine or particulate waste. Much of this waste is mineral matter that, in the context of coal, is left behind when the coal is burnt. This mineral waste matter is traditionally known in the coal industry as "ash". Ash content is an approximation of mineral matter content, but the ash content is generally quoted in coal processing because it is much more convenient and less expensive to analyse for. The term "ash content" is hereinafter used in this specification to refer to the mineral matter content.

In many coal preparation plants, fines circuits are generally poorly controlled in relation to the coarse circuits and total plant yield is thus reduced as a result. The total plant yield of coal can be improved if the ash content of the slurry can be determined at each stage of the coal separation process, especially when passing through the fines circuits. This would allow greater control over the separation process and hence improve the efficiency of the plant.

One known coal slurry ash analyser relies on nuclear sources to measure the ash content in the coal solids. However, this analyser suffers from operational problems as it is adversely affected by any entrained air in the slurry and requires frequent calibration. Furthermore, installing this analyser in a coal plant is prohibitive due to its cost and requires the implementation of health and safety measures due to the nuclear source in the analyser. As a consequence, few coal plants have installed this analyser.

OBJECT OF THE INVENTION

It is an object of the present invention to overcome or ameliorate at least one of the disadvantages of the prior art, or to provide a useful alternative.

It is an object of the invention, in its preferred form, to provide a method of online analysis and an online analyser which indirectly determines the ash content of a slurry, obviating the need for a nuclear sourced analyser and its associated problems of air entertainment and frequent calibration, and is cost effective.

SUMMARY OF THE INVENTION

According to one aspect of the invention, there is provided a method of online analysis of mineral waste content of a slurry in a mineral separation process, said method including the steps of:
  measuring the density of said slurry;
  measuring the concentration of solids in said slurry;
  calculating the density of solids in said slurry from said slurry density and said solids concentration; and
  calculating said mineral waste content from said solids density.

According to another aspect of the invention, there is provided an online analyser for mineral waste content of a slurry in a mineral separation process, said analyser including:
  a meter for measuring the density of said slurry;
  a meter for measuring the concentration of solids in said slurry; and
  a processing unit in communication with said slurry density meter and said solids concentration meter for receiving said slurry density and said solids concentration,
  wherein said processing unit calculates the density of solids in said slurry from said slurry density and said solids concentration and calculates said mineral waste content from said solids density.

Preferably, the solids density is calculated by the relationship:

$$\rho_{sol} = \frac{C_{sol}}{1 - \rho_{slurry} + C_{sol}}$$

where:
  $\rho_{sol}$ = the solids density;
  $C_{sol}$ = the concentration of solids in the slurry; and
  $\rho_{slurry}$ = the density of the slurry.

Preferably, the solids density is calculated by the relationship:

$$\rho_{sol} = \frac{C_{sol}}{\dfrac{1}{\rho_{slurry}} - \dfrac{1}{\rho_{water}} + \dfrac{C_{sol}}{\rho_{water}}}$$

where:
  $\rho_{sol}$ = the solids density;
  $\rho_{slurry}$ = the density of the slurry
  $\rho_{water}$ = the density of the water stream component of the slurry; and
  $C_{sol}$ = the concentration of solids in the slurry on a weight per weight (w/w) basis.

Preferably, the solids density is calculated by the relationship:

$$\rho_{sol} = \frac{\rho_{slurry} - ((1 - C_{sol}) \cdot \rho_{water})}{C_{sol}}$$

where:
  $\rho_{sol}$ = the solids density;

$\rho_{slurry}$=the density of the slurry;
$\rho_{water}$=the density of the water stream component of the slurry; and
$C_{sol}$=the concentration of solids in the slurry on a volume per volume (v/v) basis.

Preferably, the water stream density is calculated from at least one of the conductivity of slurry and the temperature of the slurry. Alternatively, the water stream density is measured. Preferably, the water stream density is adjusted for the temperature of the slurry. Preferably, the water stream density is adjusted for the dissolved solids concentration in the slurry. The conductivity of the slurry is preferably measured to adjust the water stream density for the dissolved solids concentration.

Preferably, the slurry density is adjusted for the dissolved solids concentration of the slurry. The conductivity of the slurry is preferably measured to calculate the dissolved solids concentration. In an alternative embodiment, the density of the water stream component of the slurry is preferably measured to adjust the slurry density for the dissolved solids concentration.

Preferably, the dissolved solids concentration is the salts concentration.

Preferably, the method includes the step of substantially removing air from the slurry before the measuring steps. Preferably, the air removing step includes inducing a downward velocity in the slurry to promote separation of air from the slurry.

Preferably, the method is performed on a batch basis to calculate the average solids density of the slurry.

Preferably, the online analyser includes a meter for measuring the conductivity of the slurry. Preferably, the slurry conductivity meter also measures the temperature of the slurry. Preferably, the slurry density meter also measures the water stream density. Preferably, the slurry density meter also measures the temperature of the slurry. Preferably, the online analyser includes a meter for measuring the temperature of the slurry.

Preferably, the online analyser includes a sump for receiving a sample of the slurry and a pump for passing the sample through the slurry density meter.

Preferably, the online analyser includes a de-aerator for removing air from the slurry. Preferably, the de-aerator includes an inlet for receiving the slurry sample and an outlet for discharging the de-aerated slurry. Preferably, the de-aerator includes a substantially vertical body to induce a downward velocity of the slurry and promote separation of air from the slurry. Preferably, the body has a portion with a relatively large inside diameter for promoting the release of air bubbles from the slurry.

Preferably, the de-aerator includes a control valve to control the slurry flowrate into the de-aerator. Preferably, the slurry density meter measures the volumetric flowrate of the slurry and communicates the measured volumetric flowrate to the flow control valve.

Preferably, the de-aerator includes a valve for releasing air from the de-aerator body. Preferably, the air release valve responds to the level of the slurry to release air from the de-aerator. Preferably, the air release valve includes a valve body with a first valve seat adjacent an inlet and a second valve seat adjacent an outlet. Preferably, the valve body includes a valve member for engaging the first and second valve seats. Preferably, the valve member responds to the level of the slurry in the valve body to release air through the valve outlet. Preferably, the valve member is engageable with the second valve seat to act as a seal. Preferably, the valve member is a ball that is buoyant in the slurry.

Preferably, the analyser includes a measuring assembly for receiving and measuring the de-aerated slurry, the assembly including a housing for storing the solids concentration meter. Preferably, the housing includes a slurry conductivity meter. Preferably, at least one of the slurry density meter and the slurry conductivity meter includes a temperature probe to measure the temperature of the slurry. Alternatively or additionally, the housing includes a temperature meter for measuring the temperature of the slurry. Preferably, the housing conveys the slurry into the slurry density meter.

The mineral waste content is preferably calculated as a proportion of the solids density. Preferably, the mineral waste content is calibrated according to a predetermined calibration curve.

The slurry may be a feed slurry, product slurry or tailings slurry in the mineral separation process.

Preferably, the mineral separation process is a flotation separation process. Preferably, the mineral separation process includes a waste product treatment process.

Preferably, the mineral extracted from the mineral separation process is coal, iron ore, copper or lead.

The invention takes advantage of the fact that the solids density is proportional to the mineral waste content of the slurry. As the solids density of the slurry can be determined by measuring at least the slurry density and the solids concentration, the mineral waste content can be derived from the solids density. Since commercially available slurry density and solids concentration meters can operate in enclosed pipe coal slurry streams, the invention in its preferred form avoids the need of nuclear sourced analyser and its associated operational problems and considerable expense.

BRIEF DESCRIPTION OF THE DRAWINGS

Preferred embodiments of the invention will now be described, by way of example only, with reference to the accompanying drawings, in which.

PREFERRED EMBODIMENT OF THE INVENTION

Figure 1:
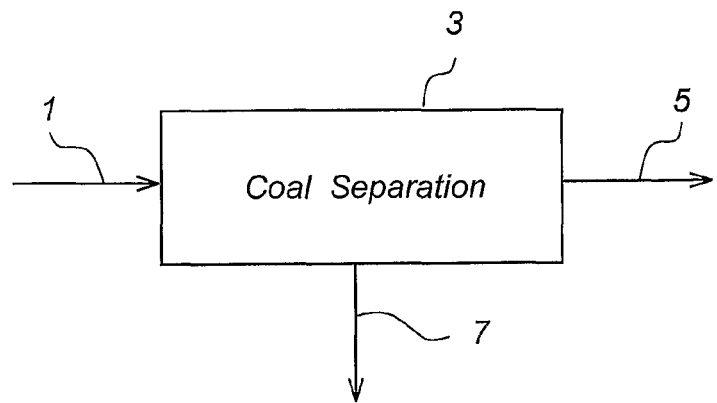
FIG. 1 is a schematic view of slurry streams in a coal separation process.
Figure 2:
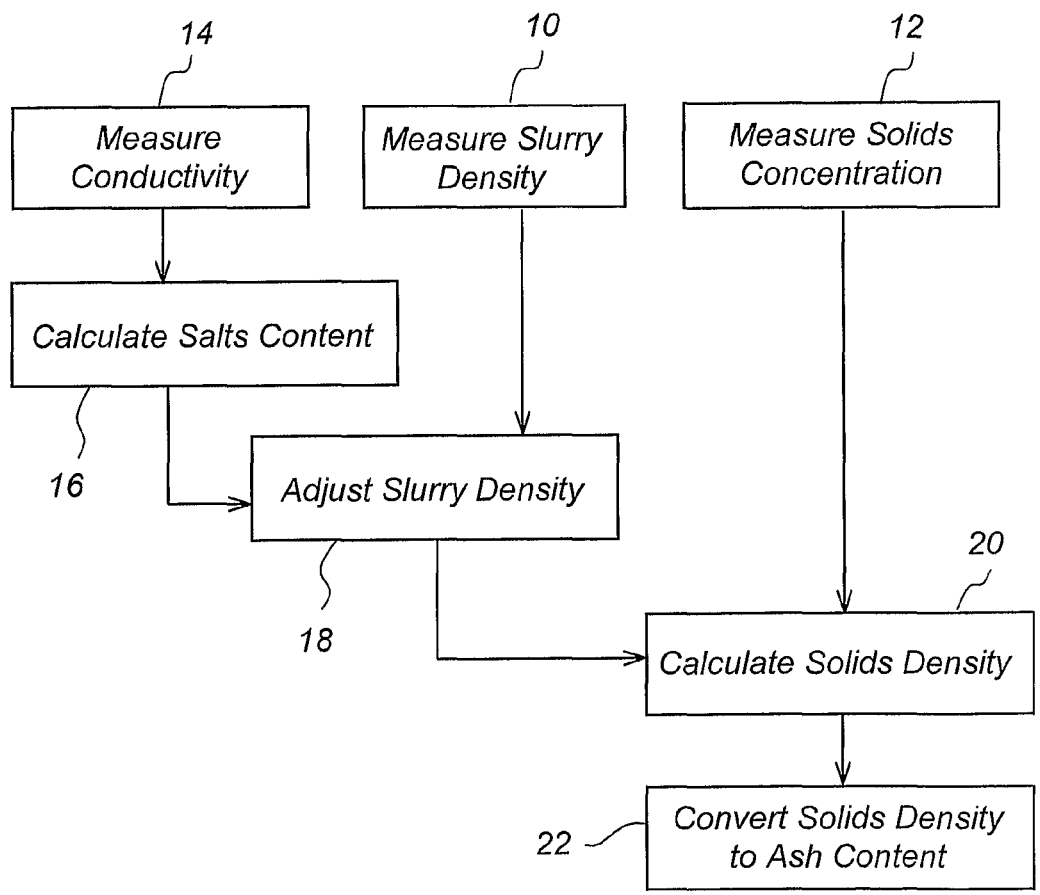
FIG. 2 is a schematic view of a method of online analysis of ash content in the coal separation process according to the invention.

Referring to the drawings, the method of online analysis of the ash content of a slurry in a coal separation process is illustrated schematically in FIGS. 1 and 2.

FIG. 1 is a basic schematic drawing of the slurry streams in a coal separation process, such as a flotation separation process. A feed slurry stream 1 containing a mixture of coal and ash is fed into the coal flotation separation process 3. After passing through the separation process 3, a product slurry stream 5 and a tailings or waste slurry stream 7 is created.

The method and the analyser of the embodiment of the invention are applicable to the feed slurry stream 1, product slurry stream 5, tailings slurry stream 7, any combination of the slurry streams, or all of the slurry streams simultaneously.

Referring now to FIG. 2, the steps in the method of online analysis of the coal slurry are shown. Initially, the density of the slurry is measured at step 10 and the concentration of solids in the slurry is measured at step 12.

In the preferred form of the invention, the salts concentration or content of the coal slurry is taken into account to improve the accuracy of the slurry density measurement. This by done by measuring the conductivity of the slurry at step 14 and then using the slurry conductivity to calculate the salts content of the slurry at step 16. The calculated salts content is in turn used to adjust the slurry density measurement at step 18.

It will be readily recognised by those skilled in the art that there is no particular order by which the slurry density, solids concentration and the slurry conductivity are measured at steps 10, 12 and 14.

The adjusted slurry density and the solids concentration measurements are then used to calculate the solids density of the slurry at step 20. The solids density is calculated by the following relationship:

$$\rho_{sol} = \frac{C_{sol}}{1 - \rho_{slurry} + C_{sol}}$$

where:
$\rho_{sol}$=the solids density of the slurry;
$C_{sol}$=the concentration of solids in the slurry; and
$\rho_{slurry}$=the density of the slurry.

The calculated solids density is then used to calculate the ash content of the slurry at step 22. The calculation of the ash content of the slurry relies on the fact that the solids density is proportional to the ash content. In practice, this may be done by using a calibration curve. The calibration curve can be produced by using the historical data of the ash content and solids density for a slurry stream of the plant.

Figure 3:
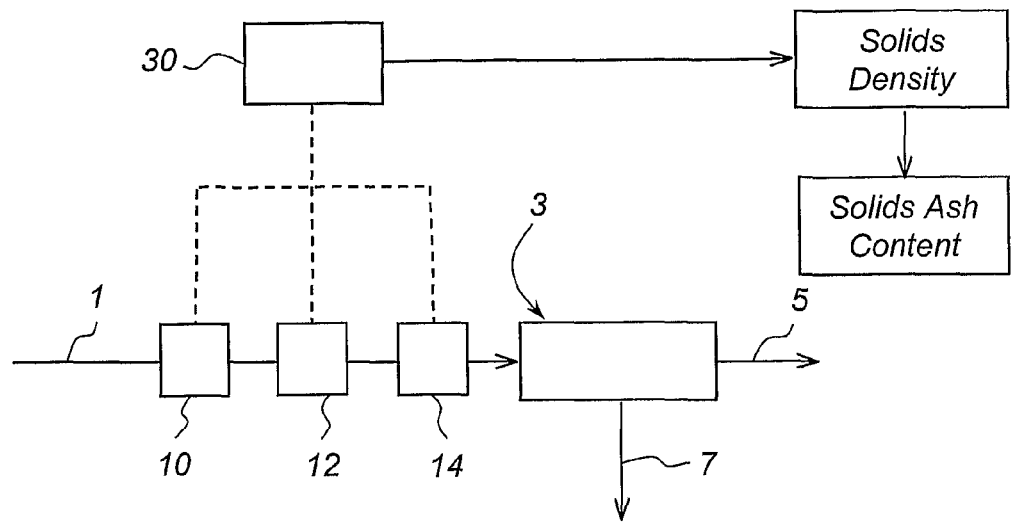
FIG. 3 is a schematic view of the method of FIG. 2 applied to the feed slurry stream of FIG. 1.

Referring to FIG. 3, an embodiment is shown where the method of FIG. 2 is applied to the feed slurry stream 1, and where corresponding features have been given the same reference numerals. In this embodiment, the slurry density measuring step 10, the solids concentration measuring step 12 and the slurry conductivity measuring step 14 are performed sequentially prior to the feed slurry stream 1 entering the coal separation process 3. The measurements taken from steps 10, 12 and 14 are transmitted to a suitable computational processing unit 30 to calculate the ash content of the feed slurry stream 1, according to the method as described above.

Commercially available meters can measure the slurry density, the solids concentration and the slurry conductivity. For example, a Micro Motion Coriolis unit can be used as the slurry density meter while a Markland 502-TP Suspended Solids Meter can be used as an ultrasonic solids concentration meter. Likewise, readily available conductivity probes can be used to measure the slurry conductivity.

An alternative to measuring slurry conductivity and correcting for the dissolved solids content at step 14 is to measure the density of the process water stream (without any suspended solids) and use this measurement to correct the slurry density. In this alternative embodiment, the slurry density meter is used to measure the water stream density.

The method of this embodiment according to the invention was tested. The past records of the washability of plant feed to a Hunter Valley coal preparation plant were examined. The 0.125 to 2 mm raw feed was collected on four days and the sample float/sunk. The ash content to solids density relationship was very good in all cases, with an average correlation coefficient $R^2$ of 0.997.

To test the frequency of calibration required, the average calibration values for the month were used, then put back into the daily results to determine the errors which would result from using monthly average calibration values for the ash content to solids density relationship. It was found that the error in the ash content was quite low, thus indicating that calibration of the embodiment is not required as frequently as in the prior art.

Alternatively, instead of using a calibration curve, the ash content can be calculated by determined factors or by assumed calculation values.

Figure 4:
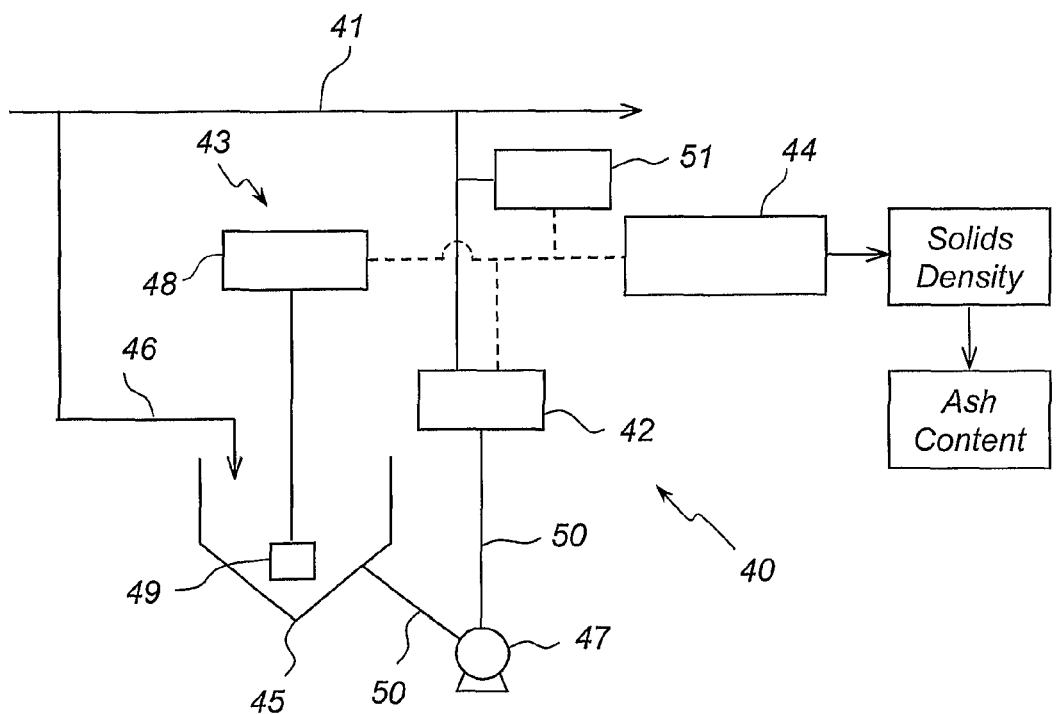
FIG. 4 is a schematic view of an online analyser in one preferred form according to the invention.

Referring to FIG. 4, a further embodiment of an online analyser 40 for a process stream 41 in accordance with the invention is shown. The online analyser 40 includes a meter 42 for measuring the density of a slurry from the process stream 41, a meter 43 for measuring the concentration of solids in the slurry, and a processing unit 44 in communication with the slurry density meter 42 and the solids concentration meter 43 for receiving the slurry density and the solids concentration measurements. The processing unit 44 calculates the density of solids in the slurry from the slurry density and the solids concentration measurements and then calculates the ash content from the solids density.

The online analyser 40 includes a sump 45 for receiving a sample 46 of the slurry taken from the process stream 41 and a pump 47 for passing the sample 46 through the slurry density meter 42, which is in the form of a Coriolis slurry density gauge. The solids concentration meter 43 is in the form of a solids concentration gauge 48 and an associated ultrasonic solids concentration probe 49.

In operation, the slurry sample 46 is fed to the sump 45 for testing. The ultrasonic probe 49 is inserted into the sump 45 and the solids concentration measured by the solids concentration gauge 48. The sample 46 is then passed through the pump 47 by a conduit 50 and through the Coriolis slurry density gauge 42 to measure the slurry density. The slurry conductivity was then measured using a handheld conductivity probe 51. The sample 46 is returned to the process stream 41, although this is not necessary.

Results of the solids concentration, slurry density and slurry conductivity measurements were recorded and then used by the processing unit 44 to calculate the solids density and subsequently the ash content.

The slurry sample 46 can be taken from any of the flotation feed, tailing and product streams.

While the slurry conductivity was measured after the sample 46 passes through the slurry density gauge 42, the conductivity probe 51 can take readings of the sample 46 before it enters the sump 45 or anywhere along the conduit 50 between the sump 45 and the slurry density gauge 42.

In testing this embodiment, samples from each of the feed, tailing and product streams were collected and sent to a laboratory for analysis, both to correlate the calculation process and to check results.

In a modification to the embodiment of FIG. 4, the slurry conductivity was not measured. Instead, the process water density (slurry without suspended solids) was measured by the slurry density gauge 42. The process water density measurement was used to adjust the slurry density measurement to take into account the presence of dissolved salts. In this modification, the need for the conductivity probe 51 is removed, resulting in a simpler and more efficient online analyser.

In other embodiments, the solids density can be calculated using a different relationship to that described in relation to the previous embodiments. For example, if the water stream density is measured, or derived from the temperature of the slurry and/or the slurry conductivity, then the solids density can be calculated by the relationship:

$$\rho_{sol} = \frac{C_{sol}}{\frac{1}{\rho_{slurry}} - \frac{1}{\rho_{water}} + \frac{C_{sol}}{\rho_{water}}}$$

where:
$\rho_{sol}$=the solids density;
$\rho_{slurry}$=the density of the slurry;
$\rho_{water}$=the density of the water stream; and
$C_{sol}$=the concentration of solids in the slurry on a weight per weight (w/w) basis.

In another example, the solids density can be calculated by the relationship:

$$\rho_{sol} = \frac{\rho_{slurry} - ((1 - C_{sol}) \cdot \rho_{water})}{C_{sol}}$$

where:
$\rho_{sol}$=the solids density;
$\rho_{slurry}$=the density of the slurry;
$\rho_{water}$=the density of the water stream; and
$C_{sol}$=the concentration of solids in the slurry on a volume per volume (v/v) basis.

In both of these relationships, the water stream density $\rho_{water}$ can be adjusted for the temperature of the slurry and the dissolved solids concentration in order to improve the accuracy of the calculation of the solids density. The slurry conductivity can be measured to perform this adjustment. Similarly, the slurry density can be adjusted for the dissolved solids concentration. If the amount of dissolved solids is minimal, or a rough calculation of the solids density is only required, then this adjustment may not be required.

It will be appreciated by one skilled in the art that the solids density can be calculated with the relationships described above using relative density (Rd) or specific gravity (Sg), instead of density ($\rho$). Ordinarily, the various densities are measured in tonnes per cubic meter (t/m$^3$), although they may be expressed in other suitable units.

In addition, the analysis may be conducted on a batch basis to calculate the average solids density of any large slurry stream within a plant.

Figure 5:
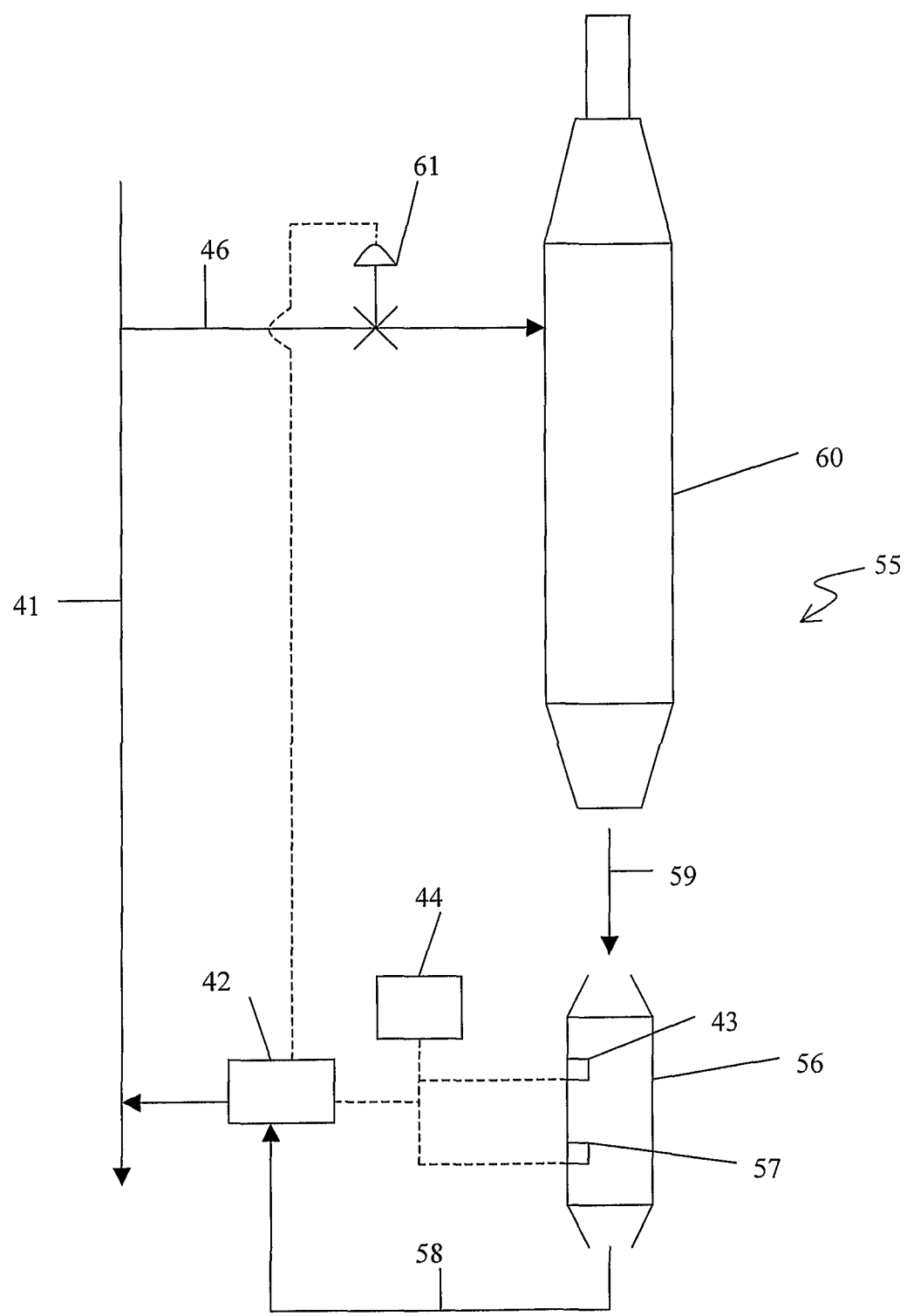
FIG. 5 is a schematic view of an online analyser in another preferred form according to the invention.

A further embodiment of the online analyser according to the invention is illustrated in FIG. 5, where corresponding features have been given the same reference numerals.

In this embodiment, the online analyser 55 includes a longitudinal measuring tube 56 for the solids concentration meter 43 and a slurry conductivity probe 57. The tube 56 provides a stable environment for the operation of these meters. A conduit 58 fluidly connects the tube 56 with the Coriolis slurry density gauge 42. Similarly, a conduit 59 fluidly connects the tube 56 with a de-aerator 60, which removes air from the slurry sample 46 to prevent erroneous readings caused by the presence of air in the slurry sample 46. A flow control valve 61 is fitted to the de-aerator 60 to ensure that there is a constant slurry flowrate and velocity throughout the analyser 55. In this embodiment, the Coriolis slurry density gauge 42 also measures the volumetric flowrate of the slurry through the tube 56, which is used to operate the flow control valve 61.

In operation, a slurry sample 46 is diverted from the process slurry stream 41 into the de-aerator 60. Air is removed from the slurry in the de-aerator 60. The conduit 59 then conveys the de-aerated slurry to the measuring tube 56, where the solids concentration meter 43 and the slurry conductivity probe 57 measure the solids concentration and conductivity of the slurry. In the embodiment, both the solids concentration meter 43 and the slurry conductivity probe 57 include temperature probes (not shown) to measure the temperature of the slurry. Alternatively, a separate temperature meter can be provided in the measuring tube 56. These measurements are sent to the processing unit 44. The slurry is then conveyed by the conduit 58 into the Coriolis slurry density gauge 42, which measures the density, volumetric flowrate and water stream density of the slurry. These measurements are also sent to the processing unit 44, which calculates the solids density $\rho_{sol}$ according to any one the above described relationships and then derives the ash content from the solids density. After exiting the Coriolis slurry density gauge 42, the slurry is then returned to the process slurry stream 41, if required.

Figure 6:
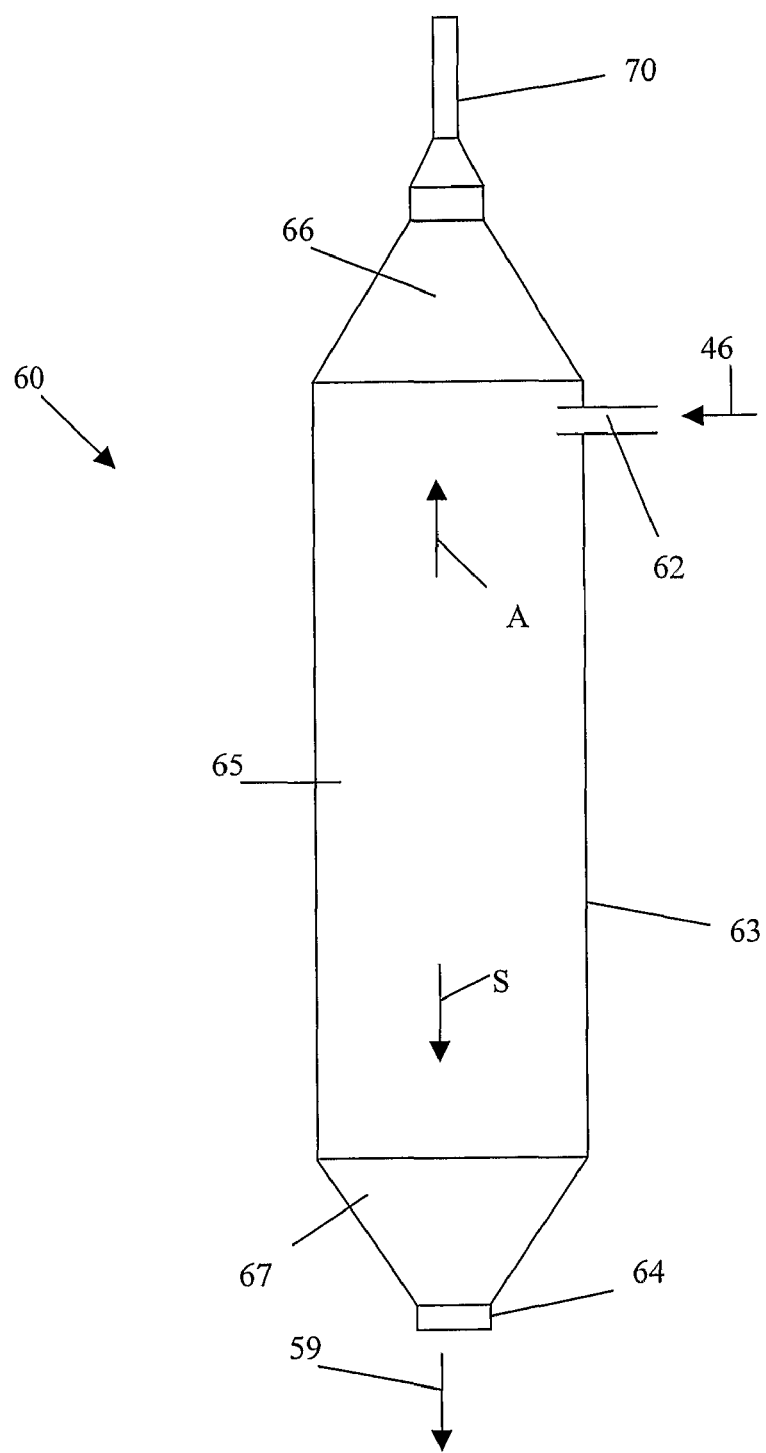
FIG. 6 is a sectional view of the de-aerator used in the online analyser of FIG. 5.

The de-aerator 60 will now be described in greater detail with reference to FIGS. 6 and 7. Referring to FIG. 6, the de-aerator 60 includes an inlet 62 for receiving the slurry from the sample 46, a cylindrical body 63 and an outlet 64 for de-aerated slurry to exit the de-aerator 60 into the conduit 59. The de-aerator 60 is arranged substantially vertical with respect to the inlet 62 to induce a downward velocity in the slurry and remove air from the slurry. The cylindrical body 63 has a central portion 65, with a relatively large inside diameter, and an upper end portion 66 and a lower end portion 67, each with a progressively narrowing inside diameter. As the central portion 65 has a relatively large inside diameter, and hence relatively large cross-sectional area, the downward velocity of the slurry is reduced. Consequently, fine air bubbles rise in the slurry, as indicated by arrow A, and then the air is released from the de-aerator 60 by an air release valve 70 located at the upper end portion 66. At the same time, the de-aerated slurry descends, as indicated by arrow S, toward the lower end portion 67 and exits the outlet 64 into the conduit 59.

Figure 7:
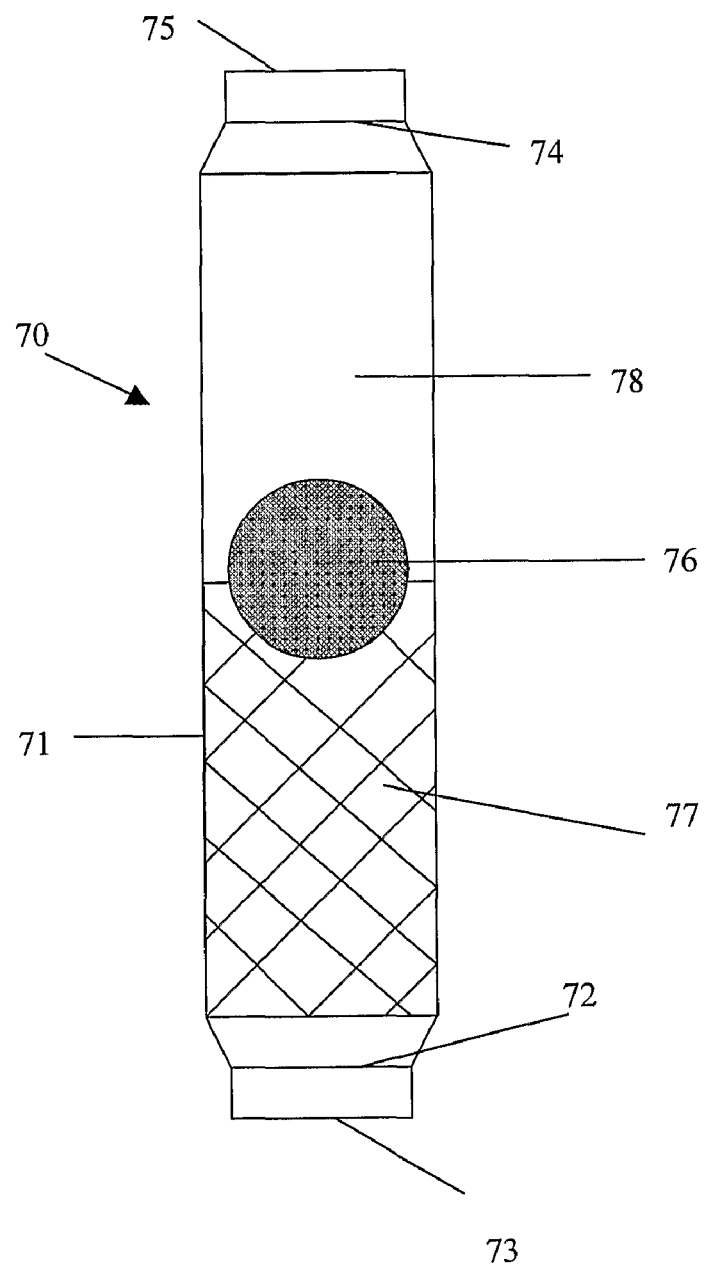
FIG. 7 is a sectional view of the air release valve use in the de-aerator of FIG. 6.

Referring to FIG. 7, the air release valve 70 includes a valve body 71 with a first valve seat 72 adjacent an inlet 73 and a second valve seat 74 adjacent an outlet 75. A valve member is the form of a ball 76 is located in the valve body 71 between the valve seats 72 and 74 for engagement therewith. The ball 76 responds to the level of the slurry in the valve body 71 to release air through the valve outlet 75, and is engageable with the second valve seat 74 to act as a seal. The air release valve 70 works on a "floating ball" principle. That is, the ball 76 in its rest state engages the first valve seat 72. As the slurry sample 46 is fed into the de-aerator body 63, the level of slurry rises and enters the inlet 73. As the ball 76 is buoyant in the slurry 77, it is lifted off the first valve seat 72. Since the inside diameter of the valve body 71 is greater than the diameter of the valve seats 72 and 74, air 78 is able to escape through the outlet 75. If the level of the slurry 77 continues to rise, then the ball 76 also rises up through the valve body 71. When the level of the slurry 77 reaches the upper end of the valve body 71, the ball 76 engages the second valve seat 74 and acts as a seal to prevent the slurry 77 from escaping the de-aerator 60. When the level of the slurry subsides, the ball 76 descends toward its rest position in engagement with the first valve seat 72.

In other modifications to this embodiment, the online analyser 55 may include a feed sump for feeding the slurry sample into the de-aerator 60. Alternatively, the slurry sample can be fed directly into the measuring tube 56. It will also be appreciated that although the tube 56 and the de-aerator 60 have been described as having substantially tubular or cylindrical bodies, they may be embodied in other suitable cross-sectional shapes, including triangular, circular, rectangular, prismatic and other geometrical cross-sections.

As discussed above, the method of online analysis and the online analyser can be used in other mineral separation processes besides a coal flotation separation process. It is envisaged that the method and the analyser according to the invention can be used with a variety of other separation processes and can be extended to other mineral ores such as iron ore, copper and lead.

It should be also noted that the adjustment of the slurry density by measuring the slurry conductivity and calculating the salts content pertains only to a coal slurry. Consequently, it should be recognised that for other minerals such as iron ore, copper and lead, it may not be necessary to adjust the slurry density. That is, steps 14, 16 and 18 may not be required in other applications of the invention.

Although the invention has been described with reference to a specific example, it will be appreciated by those skilled in the art that the invention may be embodied in many other forms.

The invention claimed is:

1. A method of online analysis of mineral waste content of a slurry in a mineral separation process, said method comprising:
measuring the density of said slurry;
measuring the concentration of solids in said slurry;
calculating, using a processing unit, the density of solids in said slurry from said slurry density and said solids concentration; and
calculating, using the processing unit, said mineral waste content from said solids density.

2. The method of claim 1, wherein the solids density is calculated by the relationship:

$$\rho_{sol} = \frac{C_{sol}}{1 - \rho_{slurry} + C_{sol}}$$

where:
$\rho_{sol}$=the solids density;
$C_{sol}$=the concentration of solids in the slurry; and
$\rho_{slurry}$=the density of the slurry.

3. The method of claim 1, wherein the solids density is calculated by the relationship:

$$\rho_{sol} = \frac{C_{sol}}{\frac{1}{\rho_{slurry}} - \frac{1}{\rho_{water}} + \frac{C_{sol}}{\rho_{water}}}$$

where:
$\rho_{sol}$=the solids density;
$\rho_{slurry}$=the density of the slurry;
$\rho_{water}$=the density of the water stream component of the slurry; and
$C_{sol}$=the concentration of solids in the slurry on a weight per weight basis.

4. The method of claim 3, wherein the water stream density is calculated from at least one of the conductivity of slurry and the temperature of the slurry.

5. The method of claim 3, wherein the water stream density is measured.

6. The method of claim 5, wherein the water stream density is adjusted for the temperature of the slurry.

7. The method of claim 5, wherein the water stream density is adjusted for the dissolved solids concentration of the slurry.

8. The method of claim 7, wherein the water stream density is adjusted by measuring the slurry conductivity of the slurry.

9. The method of claim 1, wherein the solids density is calculated by the relationship:

$$\rho_{sol} = \frac{\rho_{slurry} - ((1 - C_{sol}) \cdot \rho_{water})}{C_{sol}}$$

where:
$\rho_{sol}$=the solids density;
$\rho_{slurry}$=the density of the slurry;
$\rho_{water}$=the density of the water stream component of the slurry; and
$C_{sol}$=the concentration of solids in the slurry on a volume per volume basis.

10. The method of claim 1, wherein the slurry density is adjusted for the dissolved solids concentration of the slurry.

11. The method of claim 10, wherein the conductivity of the slurry is measured to calculate the dissolved solids concentration.

12. The method of claim 10, wherein the water stream density is measured to adjust the slurry density for the dissolved solids concentration.

13. The method of claim 10, wherein the dissolved solids concentration is the salts concentration.

14. The method of claim 1, further including the step of substantially removing air from the slurry before the measuring steps.

15. The method of claim 14, wherein the air removing step includes inducing a downward velocity in the slurry to promote separation of air from the slurry.

16. The method of claim 1, the slurry is measured on a batch basis to calculate the average solids density of the slurry.

17. The method of claim 1, wherein the mineral waste content is calculated as a proportion of the solids density.

18. The method of claim 17, wherein the mineral waste content is calibrated according to a predetermined calibration curve.

19. The method of claim 1, wherein the slurry is at least one of a feed slurry, product slurry or tailings slurry in the mineral separation process.

20. The method of claim 1, wherein the mineral separation process is a flotation separation process.

21. The method of claim 20, wherein the mineral separation process includes a waste product treatment process.

22. The method of claim 1, wherein the mineral extracted from the mineral separation process is coal, iron ore, copper or lead.

23. An online analyzer for mineral waste content of a slurry in a mineral separation process, said analyzer including:
a slurry density meter for measuring the density of said slurry;
a solids concentration meter for measuring the concentration of solids in said slurry; and a processing unit in communication with said slurry density meter and said solids concentration meter for receiving said slurry density and said solids concentration, wherein said processing unit calculates the density of solids in said slurry from said slurry density and said solids concentration and calculates said mineral waste content from said solids density.

24. The online analyzer of claim 23, further including a meter for measuring the conductivity of the slurry.

25. The online analyzer of claim 24, wherein the slurry conductivity meter also measures the temperature of the slurry.

26. The online analyzer of claim 23, wherein the slurry density meter also measures the water stream density.

27. The online analyzer of claim 23, wherein the slurry density meter also measures the temperature of the slurry.

28. The online analyzer of claim 23, further including a meter for measuring the temperature of the slurry.

29. The online analyzer of claim 23, further including a sump for receiving a sample of the slurry and a pump for passing the sample through the slurry density meter.

30. The online analyzer of claim 23, further including a de-aerator for removing air from the slurry.

31. The online analyzer of claim 30, wherein the de-aerator includes an inlet for receiving the slurry, and an outlet for discharging de-aerated slurry and a substantially vertical body to induce a downward velocity of the slurry and promote separation of air from the slurry.

32. The online analyzer of claim 31, wherein the body has a portion with a relatively large inside diameter for promoting the release of air bubbles from the slurry.

33. The online analyzer of claim 30, wherein the de-aerator includes a flow control valve to control the slurry flowrate into the de-aerator.

34. The online analyzer of claim 33, wherein the slurry density meter measures the volumetric flowrate of the slurry and communicates the measured volumetric flowrate to the flow control valve.

35. The online analyzer of claim 30, wherein the de-aerator includes a valve for releasing air from the de-aerator.

36. The online analyzer of claim 35, wherein the air release valve responds to the level of the slurry to release air from the de-aerator.

37. The online analyzer of claim 35, wherein the air release valve includes a valve body with a first valve seat adjacent an inlet and a second valve seat adjacent an outlet, and a valve member for engaging the first and second valve seats.

38. The online analyzer of claim 37, wherein the valve member responds to the level of the slurry to release air through the valve outlet.

39. The online analyzer of claim 37, wherein the valve member is engageable with the second valve seat to act as a seal.

40. The online analyzer of claim 37, wherein the valve member is a ball that is buoyant in the slurry.

41. The online analyzer of claim 30, further including a measuring assembly for receiving and measuring the de-aerated slurry, the assembly including a housing for storing the solids concentration meter.

42. The online analyzer of claim 41, wherein the housing includes a slurry conductivity meter.

43. The online analyzer of claim 41, wherein at least one of the slurry density meter and the slurry conductivity meter includes a temperature probe to measure the temperature of the slurry.

44. The online analyzer of claim 41, wherein the housing includes a temperature meter for measuring the temperature of the slurry.

45. The online analyzer of claim 41, wherein the housing conveys the slurry into the slurry density meter.

46. The online analyzer of claim 23, wherein the slurry density meter is a Coriolis slurry density gauge.

47. The online analyzer of claim 23, wherein the solids concentration meter is a solids concentration gauge, and includes an associated ultrasonic solids concentration probe.

48. The online analyzer of claim 23, wherein the slurry conductivity meter is a handheld conductivity probe.

49. The online analyzer of claim 23, wherein multiple samples are taken from the slurry on a batch basis to determine an average solids density of the slurry.

50. The online analyzer of claim 23, wherein the mineral waste content is calculated as a proportion of the solids density.

51. The online analyzer of claim 50, wherein the mineral waste content is calibrated according to a predetermined calibration curve.

52. The online analyzer of claim 23, wherein the slurry is at least one of a feed slurry, product slurry or tailings slurry in the mineral separation process.

53. The online analyzer of claim 23, wherein the mineral separation process is a flotation separation process.

54. The online analyzer of claim 53, wherein the mineral separation process includes a waste product treatment process.

55. The online analyzer of claim 23, wherein the mineral extracted from the mineral separation process is coal, iron ore, copper or lead.

56. A system for online analysis of the mineral waste content of a slurry in a mineral separation process, said system comprising:

a slurry density measuring device for measuring the density of said slurry;

a solids concentration measuring device for measuring the concentration of solids in said slurry; and a processing unit in communication with said slurry density measuring device and said solids concentration measuring device for receiving said slurry density and said solids concentration, wherein said processing unit calculates the density of solids in said slurry from said slurry density and said solids concentration and calculates said mineral waste content from said solids density.

* * * * *